United States Patent [19]

Kranz et al.

[11] Patent Number: 4,904,798
[45] Date of Patent: Feb. 27, 1990

[54] (4-AMINO-2-HYDROXYPHENYL-1-OXOISOINDOLENINES, PREPARATION THEREOF AND HYDROLYSIS THEREOF TO 2-(4-AMINO-2-HYDROXYBENZOYL)BENZOIC ACIDS

[75] Inventors: Joachim Kranz; Bernd Landmann, both of Ludwigshafen; Udo Mayer, Frankenthal, all of Fed. Rep. of Germany

[73] Assignee: BASF Aktiengesellschaft, Ludwigshafen, Fed. Rep. of Germany

[21] Appl. No.: 295,462

[22] Filed: Jan. 10, 1989

[30] Foreign Application Priority Data

Jan. 12, 1988 [DE] Fed. Rep. of Germany ....... 3800577

[51] Int. Cl.$^4$ ............... C07D 413/00; C07D 405/00; C07D 409/00
[52] U.S. Cl. ................................. 548/472; 544/144; 546/200; 548/467
[58] Field of Search ............... 548/472, 467, 472; 562/500; 544/144; 546/200

[56] References Cited

U.S. PATENT DOCUMENTS 4,505,921 3/1985 Beregi et al. ............... 548/472

Primary Examiner—Mukund J. Shah
Assistant Examiner—Deborah D. Carr
Attorney, Agent, or Firm—Oblon, Spivak, McClelland, Maier & Neustadt

[57] ABSTRACT

Isoindolenines of the general formula (I)

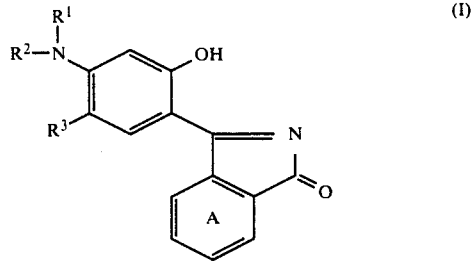

where
$R^1$ is hydrogen, unsubstituted or chlorine-, hydroxyl-phenyl- or cyano-substituted $C_1$–$C_{12}$-alkyl or $C_5$–$C_8$-cycloalkyl or unsubstituted or chlorine- or methyl-substituted phenyl,
$R^2$ is hydrogen or unsubstituted or chlorine-, hydroxyl-, phenyl- or cyano-substituted $C_1$–$C_6$-alkyl, or is morpholino, pyrrolidino or piperidino, and
$R^3$ is hydrogen or methyl and the benzene ring A may be substituted by from 1 to 4 chlorines, 1 or 2 $C_1$–$C_4$-alkyls or 1 nitro, are obtained by condensing 3-aminophenols of the formula (II)

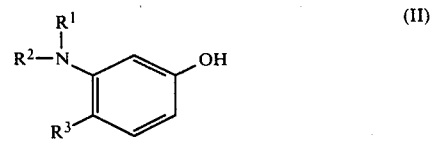

with 3-amino-1-oxoisoindolenines of the general formula (III)

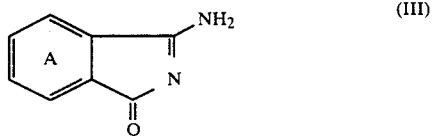

in the presence of acids, and are hydrolyzible in very good yields into benzoylbenzoic acids (IV)

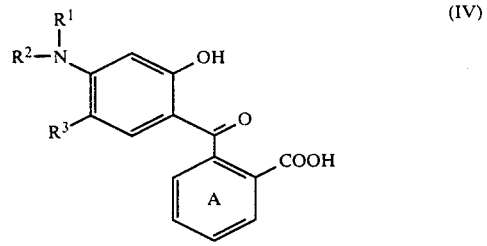

which are very difficult, if not impossible, to prepare by prior art methods.

17 Claims, No Drawings

(4-AMINO-2-HYDROXYPHENYL-1-OXOISOINDOLENINES, PREPARATION THEREOF AND HYDROLYSIS THEREOF TO 2-(4-AMINO-2-HYDROXYBENZOYL)BENZOIC ACIDS 2-(4-Amino-2-hydroxybenzoyl)benzoic acids (IV) are important intermediates in the production of fluorans and rhodamines. The acids (IV) are prepared in the prior art by reacting 3-aminophenols with substituted or unsubstituted phthalic anhydrides (DE-A-85,931; DE-A-2,322,131 and 2,444,297; US-A-4,515,971; DE-A-3,415,331; EP-A-176,161; JP-A-70,350/1987). In this reaction, rhodamines are formed as by-products. The desired benzoylbenzoic acids (IV) are frequently only formed in low yields. Certain benzoylbenzoic acids are not preparable at all in this way.

It is an object of the present invention to provide an industrially readily applicable process for preparing benzoylbenzoic acids in good to high yields and in high purity.

We have found that this object is achieved with a process for preparing benzoylbenzoic acids (IV) from novel isoindolenine compounds (I).

The present invention accordingly provides novel isoindolenines of the general formula (I)

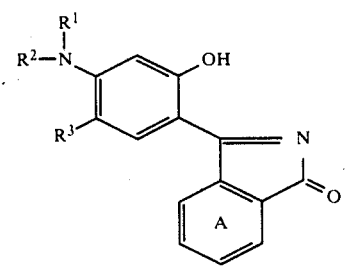

where
$R^1$ is hydrogen, unsubstituted or chlorine-, hydroxyl-, phenyl- or cyano-substituted $C_1$–$C_{12}$-alkyl or $C_5$–$C_8$-cycloalkyl or unsubstituted or chlorine- or methyl-substituted phenyl,
$R^2$ is hydrogen or unsubstituted or chlorine-, hydroxyl-, phenyl- or cyano-substituted $C_1$–$C_6$-alkyl, or

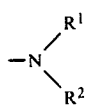

is morpholino, pyrrolidino or piperidino, and
$R^3$ is hydrogen or methyl and the benzene ring A may be substituted by from 1 to 4 chlorines, 1 or 2 $C_1$–$C_4$-alkyls or 1 nitro.

The present invention further provides a process for preparing an isoindolenine of the general formula I, which comprises condensing an aminophenol of the general formula (II)

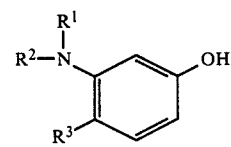

where
$R^1$ is hydrogen, unsubstituted or chlorine-, hydroxyl-, phenyl- or cyano-substituted $C_1$–$C_{12}$-alkyl or $C_5$–$C_8$-cycloalkyl or unsubstituted or chlorine- or methyl-substituted phenyl,
$R^2$ is hydrogen or unsubstituted or chlorine-, hydroxyl-, phenyl- or cyano-substituted $C_1$–$C_6$-alkyl, or is morpholino, pyrrolidino or piperidino, and
$R^3$ is hydrogen or methyl,
with a 3-amino-1-oxoindolenine of the general formula (III)

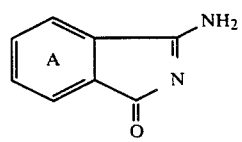

where the benzene ring A may be substituted by from 1 to 4 chlorines, 1 or 2 $C_1$–$C_4$-alkyls or 1 nitro, in the presence of an acid.

The isoindolenines I according to the invention are advantageously prepared by condensing the 3-aminophenol (II) with the 3-amino-1-oxoisoindolenine (III) in an organic solvent in the presence of one equivalent of an acid at from 60° to 140° C. Suitable solvents are for example dimethylformamide, toluene, xylene, chlorobenzene, dichlorobenzene and straight-chain or branched alkanols. Preferred solvents are dimethylformamide and isobutanol. The acid used can be for example hydrochloric acid, sulfuric acid, phosphoric acid or p-toluenesulfonic acid. Preferably, the condensation is carried out with the isoindolenine hydrochloride of the formula (IIIa)

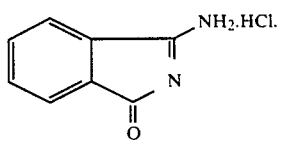

The novel isoindolenines (I) are obtained in a high yield and are convertible in a high yield into the corresponding benzoylbenzoic acids of the general formula (IV)

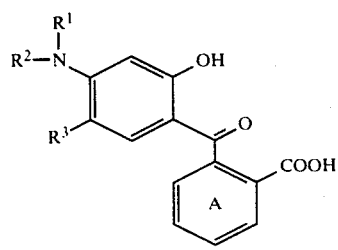

where $R^1$, $R^2$, $R^3$ and A are each as defined above.

Accordingly, the present invention also provides a process for preparing a benzoylbenzoic acid (IV) by hydrolyzing a compound of the general formula (I). The hydrolysis may be carried out under acidic or preferably under alkaline conditions. The benzoylbenzoic acids (IV) obtained are very pure and uncontaminated by rhodamines. Some benzoylbenzoic acids are not preparable at all or only in a small yield by prior art methods (condensation of the aminophenol with phthalic anhydride).

The hydrolysis is in general effected by heating (I) in a dilute acid or preferably in an aqueous alkali metal hydroxide solution; if the latter, the benzoylbenzoic acid dissolves.

The acid used is a from 5 to 30% strength by weight acid such as sulfuric acid or hydrochloric acid.

The base used is preferably a from 5 to 40% strength by weight aqueous solution of an alkali metal hydroxide or alkaline earth metal hydroxide, in particular sodium hydroxide solution or potassium hydroxide solution. The acid (IV) is precipitated from the alkaline solution by acidification and isolated in a conventional manner.

The invention will be additionally illustrated by the Examples below. Parts and percentages are by weight.

EXAMPLE 1

(a) 183 parts of 3-amino-1-oxoisoindolenine hydrochloride are added a little at a time to a solution of 151 parts of 3-ethylamino-4-methylphenol in 240 parts of dimethylformamide at 120° C. The mixture is heated at 120° C. for one hour. After cooling down, the solid is filtered off with suction, washed with 200 parts of ethanol and dried at 60° C. under reduced pressure leaving 263 parts of 3-(4'-ethylamino-2'-hydroxy-5'-methylphenyl)-1-oxoisoindolenine as brown crystals of melting point 258°–260° C.

| $C_{17}H_{16}N_2O_2$ MW 280.33 | | | | |
|---|---|---|---|---|
| | C | H | N | O |
| calculated | 72.84 | 5.75 | 9.99 | 11.41 |
| found | 72.6 | 5.9 | 10.2 | 11.4 |

(b) 28 parts of 3-(4'-ethylamino-2'-hydroxy-5'-methylphenyl)-1-oxoisoindolenine are refluxed in 118 parts of 20% strength potassium hydroxide solution for 5 hours. The solution is filtered and the filtrate is cooled and brought to pH 4.5 with concentrated hydrochloric acid. The precipitated solid is filtered off with suction, washed with water and dried at 60° C. under reduced pressure leaving 23.5 parts of 2-(4'-ethylamino-2'-hydroxy-5'-methylbenzoyl)benzoic acid as a yellowish solid of melting point 200°–202° C.

| $C_{17}H_{17}NO_4$ MW 299.33 | | | | |
|---|---|---|---|---|
| | C | H | N | O |
| calculated | 68.22 | 5.72 | 4.68 | 21.38 |
| found | 68.1 | 5.7 | 4.7 | 21.2 |

EXAMPLE 2

(a) 18.3 parts of 3-amino-1-oxoisoindolenine hydrochloride are added a little at a time to a solution of 17.9 parts of 3-morpholinophenol in 24 parts of isobutanol at 100° C. The mixture is heated at 100° C. for 5 hours. After cooling down, the solid is filtered off with suction, washed with isobutanol and dried at 60° C. under reduced pressure, leaving 24.1 parts of 3-(4'-morpholino-2'-hydroxyphenyl)-1-oxoisoindolenine as a reddish brown solid. A sample is recrystallized from dimethylformamide in reddish brown needles of melting point 290°–292° C.

| $C_{18}H_{16}N_2O_2$ MW 308.34 | | | | |
|---|---|---|---|---|
| | C | H | N | O |
| calculated | 70.12 | 5.23 | 9.09 | 15.57 |
| found | 69.9 | 5.4 | 9.2 | 15.5 |

(b) 15.4 parts of 3-(4'-morpholino-2'-hydroxyphenyl)-1-oxoisoindolenine are refluxed in 60 parts of 20% strength sodium hydroxide solution for 1 hour. The solution is filtered, and the filtrate is cooled down and brought to pH 4.5 with concentrated hydrochloric acid. The precipitated solid is filtered off with with suction, washed with water and dried at 60° C. under reduced pressure, leaving 10.7 parts of 2-(4'-morpholino-2'-hydroxybenzoyl)benzoic acid as a yellowish solid of melting point 184°–187° C.

| $C_{18}H_{17}NO_5$ MW 327.34 | | | | |
|---|---|---|---|---|
| | C | H | N | O |
| calculated | 66.05 | 5.23 | 4.28 | 24.44 |
| found | 65.9 | 5.0 | 4.0 | 24.4 |

The procedure of Examples 2(a) and 2(b) is followed to prepare the substituted 1-oxoisoindolenines (VI) and benzoylbenzoic acids (VII).

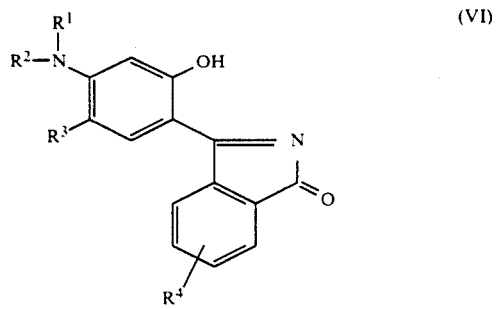

(VI)

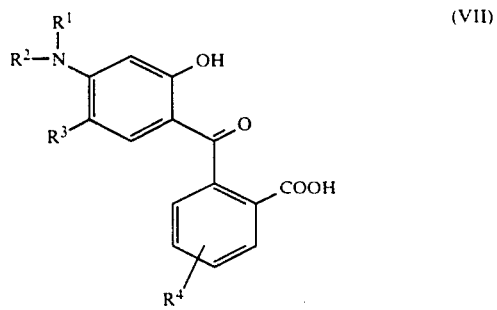

(VII)

The compounds are characterized in Table 1 by their melting points.

TABLE 1

| No. | R¹ | R² | R³ | R⁴ | (VI) mp. [°C.] | (VII) mp. [°C.] |
|---|---|---|---|---|---|---|
| 3 | ⟨H⟩ | —H | —H | —H | 242–246 | 126–128 |

TABLE 1-continued

| No. | R¹ | R² | R³ | R⁴ | (VI) mp. [°C.] | (VII) mp. [°C.] |
|---|---|---|---|---|---|---|
| 4 |  | —CH₃ | —H | —H | 227–230 (dec.) | 125–130 |
| 5 | —CH₃ | —CH₃ | —H | —H | 250–253 | 137–140 |
| 6 | —C₂H₅ | —C₂H₅ | —H | —H | 250–253 | 214–217 |
| 7 | —C₂H₄OH | —CH₃ | —H | —H | 216–218 | 102–104 |
| 8 | —(CH₂)₄— | | —H | —H | 238–242 | 159–162 |
| 9 | —CH₃ | —CH₃ | —CH₃ | —H | | 182–185 |
| 10 | —C₂H₅ | —CH₃ | —CH₃ | —H | | 152–154 |

The same method was also used to prepare the substituted 1-oxoisoindolenines (VI) and benzoylbenzoic acids (VII) listed in the following table:

TABLE 2

| No. | R¹ | R² | R³ | R⁴ |
|---|---|---|---|---|
| 11 | phenyl | —CH₃ | —H | —H |
| 12 | 4-methylphenyl | —CH₃ | —H | —H |
| 13 | 4-methylphenyl | C₂H₅ | —H | —H |
| 14 | benzyl (C₆H₅CH₂—) | H | —CH₃ | —H |
| 15 | —(CH₂)₄— | | —H | —C(CH₃)₃ |
| 16 | —(CH₂)₂—O—(CH₂)₂— | | —H | —C(CH₃)₃ |
| 17 | —(CH₂)₅— | | —H | —C(CH₃)₃ |
| 18 | —CH₃ | —CH₃ | —H | —C(CH₃)₃ |
| 19 | —C₂H₅ | —C₂H₅ | —H | —C(CH₃)₃ |
| 20 | —C₄H₉ | —C₄H₉ | —H | —H |
| 21 | (CH₃)₂CH—CH₂—CH₂— | —C₂H₅ | —H | —H |

We claim:
1. An isoindolenine of the general formula (I)

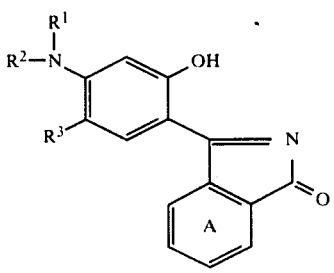

(I)

where
R¹ is hydrogen, unsubstituted or chlorine-, hydroxyl-, phenyl- or cyano-substituted C₁–C₁₂-alkyl or C₅–C₈-cycloalkyl or unsubstituted or chlorine- or methyl-substituted phenyl,
R² is hydrogen or unsubstituted or chlorine-, hydroxyl-, phenyl- or cyano-substituted C₁–C₆-alkyl, or

is morpholino, pyrrolidino or piperidino, and
R³ is hydrogen or methyl and the benzene ring A may be substituted by from 1 to 4 chlorines, 1 or 2 C₁–C₄-alkyls or 1 nitro.

2. An isoindolenine as claimed in claim 1, wherein R¹ is C₁–C₆-alkyl, benzyl, phenyl or methylphenyl.

3. An isoindolenine as claimed in claim 1, wherein R¹ is methyl or ethyl.

4. An isoindolenine as claimed in claim 2, wherein R² is hydrogen, methyl or ethyl.

5. An isoindolenine as claimed in claim 3, wherein R² is hydrogen or methyl or ethyl.

6. An isoindolenine as claimed in claim 2, wherein R³ is methyl.

7. An isoindolenine as claimed in claim 4, wherein R³ is methyl.

8. An isoindolenine as claimed in claim 5, wherein R³ is methyl.

9. An isoindolenine as claimed in claim 1, wherein

is morpholino, pyrrolidino or piperidino and R³ is hydrogen.

10. An isoindolenine as claimed in claim 6, wherein

is morpholino, pyrrolidino or piperidino and R³ is hydrogen.

11. An isoindolenine as claimed in claim 7, wherein

is morpholino, pyrrolidino or piperidino and R³ is hydrogen.

12. An isoindolenine as claimed in claim 8, wherein

is morpholino, pyrrolidino or piperidino and R³ is hydrogen.

13. An isoindolenine as claimed in claim 1, wherein the benzene ring A is unsubstituted or substituted by t-butyl.

14. An isoindolenine as claimed in claim 3, wherein the benzene ring A is unsubstituted or substituted by t-butyl.

15. An isoindolenine as claimed in claim 5, wherein the benzene ring A is unsubstituted or substituted by t-butyl.

16. An isoindolenine as claimed in claim 8, wherein the benzene ring A is unsubstituted or substituted by t-butyl.

17. An isoindolenine as claimed in claim 12, wherein the benzene ring A is unsubstituted or substituted by t-butyl.

* * * * *